(12) United States Patent
Maetzler et al.

(10) Patent No.: US 10,338,086 B2
(45) Date of Patent: Jul. 2, 2019

(54) SUPPLYING CONSUMABLE ITEMS TO AN AUTOMATED SAMPLE ANALYZER

(71) Applicant: Roche Diagnostics Operations, Inc., Indianapolis, IN (US)

(72) Inventors: Marco Maetzler, Belmont, CA (US); Liutger Joannes Franzen, Buchrain (CH); Florian Zwahlen, Zug (CH); Hans Reischauer, Arth (CH); Adrian Cojocaru, Dolj (RO); Stephan Topsakalian, Rotkreuz (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/600,089

(22) Filed: May 19, 2017

(65) Prior Publication Data
US 2017/0350912 A1    Dec. 7, 2017

(30) Foreign Application Priority Data
Jun. 6, 2016    (EP) .................................... 16173152

(51) Int. Cl.
*G01N 35/02*    (2006.01)
*G01N 35/04*    (2006.01)
(Continued)

(52) U.S. Cl.
CPC ..... *G01N 35/1002* (2013.01); *G01N 35/0099* (2013.01); *G01N 35/00663* (2013.01);
(Continued)

(58) Field of Classification Search
CPC ..... G01N 2035/0498; G01N 35/00663; G01N 35/00871; G01N 35/0099; G01N 35/04; G01N 35/1002; G06Q 10/087
See application file for complete search history.

(56) References Cited

U.S. PATENT DOCUMENTS 8,535,607 B2    9/2013   Wakamiya et al.
8,663,557 B2    3/2014   Tanoshima et al.
(Continued)

FOREIGN PATENT DOCUMENTS

| EP | 1156434 A1 | 11/2001 |
| EP | 1975624 A2 | 10/2008 |
| EP | 2546655 A1 | 1/2013 |

*Primary Examiner* — Jennifer Wecker
(74) *Attorney, Agent, or Firm* — Roche Diagnostics Operations, Inc.

(57) ABSTRACT

A method for supplying consumable items to an automated sample analyzer is presented. The automated analyzer comprises a consumable repository including two or more storage areas. Each area is configured to store a plurality of consumable items. The method comprises receiving one or more orders for analytical tests to be carried out by the analyzer, reserving consumable items corresponding to one or more sets of consumable items required for the analytical tests in a first area, switching to a second area for reserving consumable items in response to determining that a predetermined consumable item in the first area has been reserved, supplying the reserved consumable items for use in the one or more analytical tests and indicating that the first area can be replenished in response to determining that a particular consumable item of the first storage area has been used.

18 Claims, 6 Drawing Sheets

(51) Int. Cl.
  *G01N 35/10*   (2006.01)
  *G01N 35/00*   (2006.01)
  *G06Q 10/00*   (2012.01)
  *G06Q 10/08*   (2012.01)

(52) U.S. Cl.
  CPC ....... *G01N 35/00871* (2013.01); *G01N 35/04* (2013.01); *G01N 2035/0498* (2013.01); *G06Q 10/087* (2013.01)

(56) References Cited

U.S. PATENT DOCUMENTS

| | | | |
|---|---|---|---|
| 2010/0324722 A1* | 12/2010 | Fritchie | G01N 35/00732 700/214 |
| 2011/0246215 A1* | 10/2011 | Postma | G06Q 10/087 705/2 |
| 2012/0269604 A1* | 10/2012 | Baumann | G01N 35/04 414/222.01 |
| 2012/0275956 A1 | 11/2012 | Wakamiya et al. | |
| 2013/0065797 A1* | 3/2013 | Silbert | G01N 35/0099 506/39 |

\* cited by examiner

Figure 6

SUPPLYING CONSUMABLE ITEMS TO AN AUTOMATED SAMPLE ANALYZER

CROSS-REFERENCE TO RELATED APPLICATIONS

This application is a continuation of EP 16173152.6, filed Jun. 6, 2016, which is hereby incorporated by reference.

BACKGROUND

The present disclosure relates to methods for supplying consumable items to an automated sample analyzer for biological samples and apparatuses for analyzing samples including a consumable item repository.

Automated analyzers for analyzing samples (e.g., automated analyzers deployed in a clinical laboratory environment) frequently use consumable items during operation. These consumable items have to be replenished regularly to secure that the analyzers can operate properly.

For instance, some automated sample analyzers include automated pipettors which manipulate biological samples and reagents. During these operations, the analyzers might use disposable pipette tips and reaction vessels and possibly additional consumable items. Pipette tips and reaction vessels can be provided to the analyzer in racks or other containers. These containers have to be replenished by a user of the automated sample analyzer in some examples.

While operating these devices, a user might forget to replenish the consumable containers in time, or might make a mistake in the course of a refill process (e.g., replace an empty container of disposable items by another empty container). As a consequence of such errors, the analyzer might not find the consumable items needed to perform a particular scheduled analytical test at some point in time. This might lead to an increased idle time of the analyzer.

SUMMARY

According to the present disclosure, a method and apparatus for supplying consumable items to an automated sample analyzer are presented. The automated analyzer can includes a consumable repository including two or more storage areas. Each storage area can be configured to store a plurality of consumable items. The method can comprise receiving one or more orders for analytical tests to be carried out by the analyzer. Rach of the analytical tests can require a set of consumable items. The method can also comprise reserving consumable items corresponding to the one or more sets of consumable items required for the analytical tests in a first storage area of the two or more storage areas, switching to a second storage area of the two or more storage areas for reserving consumable items in response to determining that a predetermined consumable item in the first storage area has been reserved, supplying the reserved consumable items for use in the one or more analytical tests, and indicating that the first storage area can be replenished in response to determining that a particular consumable item of the first storage area has been used in the one or more analytical tests.

Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method for supplying consumable items to an automated sample analyzer is presented. The automated analyzer can comprise a consumable repository including two or more storage areas. Each storage area can be configured to store a plurality of consumable items. The method can comprise receiving one or more orders for analytical tests to be carried out by the analyzer. Each of the analytical tests can require a set of consumable items. The method can also comprise reserving consumable items corresponding to the one or more sets of consumable items required for the analytical tests in a first storage area of the two or more storage areas, switching to a second storage area of the two or more storage areas for reserving consumable items in response to determining that a predetermined consumable item in the first storage area has been reserved, supplying the reserved consumable items for use in the one or more analytical tests, and indicating that the first storage area can be replenished in response to determining that a particular consumable item of the first storage area has been used in the one or more analytical tests.

An apparatus for analyzing samples is also presented. The apparatus can comprise a consumable repository including two or more storage areas. Each storage area can be configured to store a plurality of consumable items. The apparatus can also comprise a supply device for supplying the consumable items to be used in the analysis processes and a controller configured to control the apparatus to receive one or more orders for analytical tests to be carried out by the analyzer. Each of the analytical tests can require a set of consumable items. The control can also be configured to reserve consumable items corresponding to the one or more sets of consumable items required for the analytical tests in a first storage area of the two or more storage areas, switch to a second storage area of the two or more storage areas for reserving consumable items in response to determining that a predetermined consumable item in the first storage area has been reserved, supply the reserved consumable items for use in the one or more analytical tests, and indicate that the first storage area can be replenished in response to determining that a particular consumable item of the first storage area has been used in the one or more analytical tests.

The above method and the apparatus can have one or more of the following advantages in some embodiments.

Firstly, analyzer idle time can be reduced by securing that the consumable items required to perform the scheduled analytical test are stored in the consumable repository of the analyzer at the time when the scheduled analytical test can be carried out. When using some prior art systems, a user might only be notified at the moment when an order for an analytical test arrives that a repository includes insufficient consumable items to carry out the order. In still other examples, an error message can be generated when the analyzer recognizes that a repository is empty. However, in both cases, the analyzer might not be in a state to continue with processing orders which might lead to an increased idle time of the analyzer. By reserving the consumable items in the repository of the analyzer after the orders for analytical test arrive at the analyzer, the techniques described in the present disclosure may reduce the number and duration of analyzer idle periods.

Secondly, in some examples, the techniques of the present invention can reduce the number of times a user has to interact with the analyzer to refill consumable items by indicating that a storage area of a plurality of storage areas of the analyzer can be refilled at a predetermined point in time. Similarly, in a situation where an automated replenishment device is used, the automated replenishment device can be activated upon receiving a replenishment indication. This can secure that the automated replenishment device can be used just in time and can make the use of the automated replenishment device more resource-efficient.

Thirdly, in some examples of the present disclosure, the reservation process and replenishment processes can be synchronized. In this manner, a user can replenish a storage area while the analyzer continues to supply consumable items from a different storage area of the repository. This can further reduce the idle time of the analyzer.

Fourthly, a state of the automated sample analyzer can be changed in some examples in response to the replenishment indication. For example, a storage area can be locked unless a replenishment indication is issued. This can prevent the user from interacting with the storage area (e.g., opens a drawer) while the automated sample analyzer supplies consumable items from this storage area. Consequentially, the number of operating errors can be reduced that potentially damage the analyzer or, at least, disturb the analysis process.

The term 'consumable item' can refer to any item that can be consumed by an automated sample analyzer in the course of an analysis process (including process steps which can precede or succeed an actual measurement in an analysis process). For instance, a consumable item can be a disposable which may be used only once or several times and can afterwards be disposed. However, in other examples a consumable item can be an item which can be used only once or several times by the analyzer and afterwards can be removed from the analyzer for restoration into a usable state (e.g., by washing, chemical disinfection or another cleaning procedure).

In some examples, consumable items can be parts of the instruments or devices of the automated analyzer which can be used in the analysis process and which can be regularly replaced. Example of parts of the instruments or devices which can be regularly replaced can be items which come in contact with analytes or reagents (e.g., instrument tips, filters or vessels). For example, some automated analyzers may use one or more of pipette tips, needles, reaction vessels, sample vessels or transport vessels for liquids which have to be handled in an analysis process. In some examples, the reaction vessel, the transport vessel or the sample vessel can be a cuvette, a tube, a slide, a multiwell plate or microplate.

In other examples, a consumable item may be a quantity of a substance consumed in the analysis process. For instance, a substance consumed in the analysis process can be a reagent or other type of substance supplied to a sample in the course of the analysis process, or in preparation steps for the analysis step or post-analysis steps (e.g., cleaning steps of the analyzer).

The terms 'analyzer'/'analytical work cell'/'analytical unit' as used herein can encompass any apparatus or apparatus component that can measure analytical properties of a sample, e.g., following a reaction of a sample with a reagent for obtaining a measurement value.

An analyzer can be operable to determine one or more parameters of a sample or a component thereof. For example, a parameter can be an absorption, transmittance or reflectance of the sample contained in a cuvette or other sample vessel. In other examples, a parameter can be a fluorescence of a sample after having been illuminated with excitation light. In other examples, the analyzer can include a device to measure an electro-chemical luminescence of a sample. Apart from the optical measurement devices of an analyzer discussed (e.g., to determine an absorption, transmittance, luminescence or reflectance), an analyzer can include measurement devices to determine a parameter of the sample via one or more chemical, biological, physical, or other technical procedures.

An analyzer may be operable to determine the parameter of the sample or of at least one analyte, process the determined parameter and return an obtained measurement value. The list of possible analysis results returned by the analyzer can comprise, without limitation, concentrations of the analyte in the sample, a qualitative (yes or no) result indicating the existence of the analyte in the sample (corresponding to a concentration above the detection level), optical parameters, DNA or RNA sequences, data obtained from mass spectroscopy of proteins or metabolites and physical or chemical parameters of various types.

An analytical work cell may comprise units for pipetting, dosing, and mixing of samples and/or reagents. The analyzer may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analyzer may comprise a process and detection system whose workflow can be optimized for certain types of analysis. Examples of such analyzers can be clinical chemistry analyzers, coagulation chemistry analyzers, immunochemistry analyzers, urine analyzers, hematology analyzers, nucleic acid analyzers, used to detect the result of chemical or biological reactions or to monitor the progress of chemical or biological reactions.

The term 'sample' can refer to material(s) that may potentially contain an analyte of interest. The sample can be derived from a biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The biological sample can be pretreated prior to use, such as preparing plasma from blood. Methods of treatment can involve centrifugation, filtration, distillation, dilution, concentration and/or separation of sample components including analytes of interest, inactivation of interfering components, and the addition of reagents. A sample may be used directly as obtained from the source or used following a pretreatment to modify the character of the sample. In some embodiments, an initially solid or semi-solid biological material can be rendered liquid by dissolving or suspending it with a suitable liquid medium. In some examples, the sample can be suspected to contain a certain antigen or nucleic acid.

In connection with FIG. 1 and FIG. 2, embodiments of the supplying consumable items to an automated sample analyzer will be discussed. Subsequently, in connection with FIG. 3 to FIG. 6, different embodiments for analyzing sample according to the present disclosure will be treated in more detail.

Figure 1:
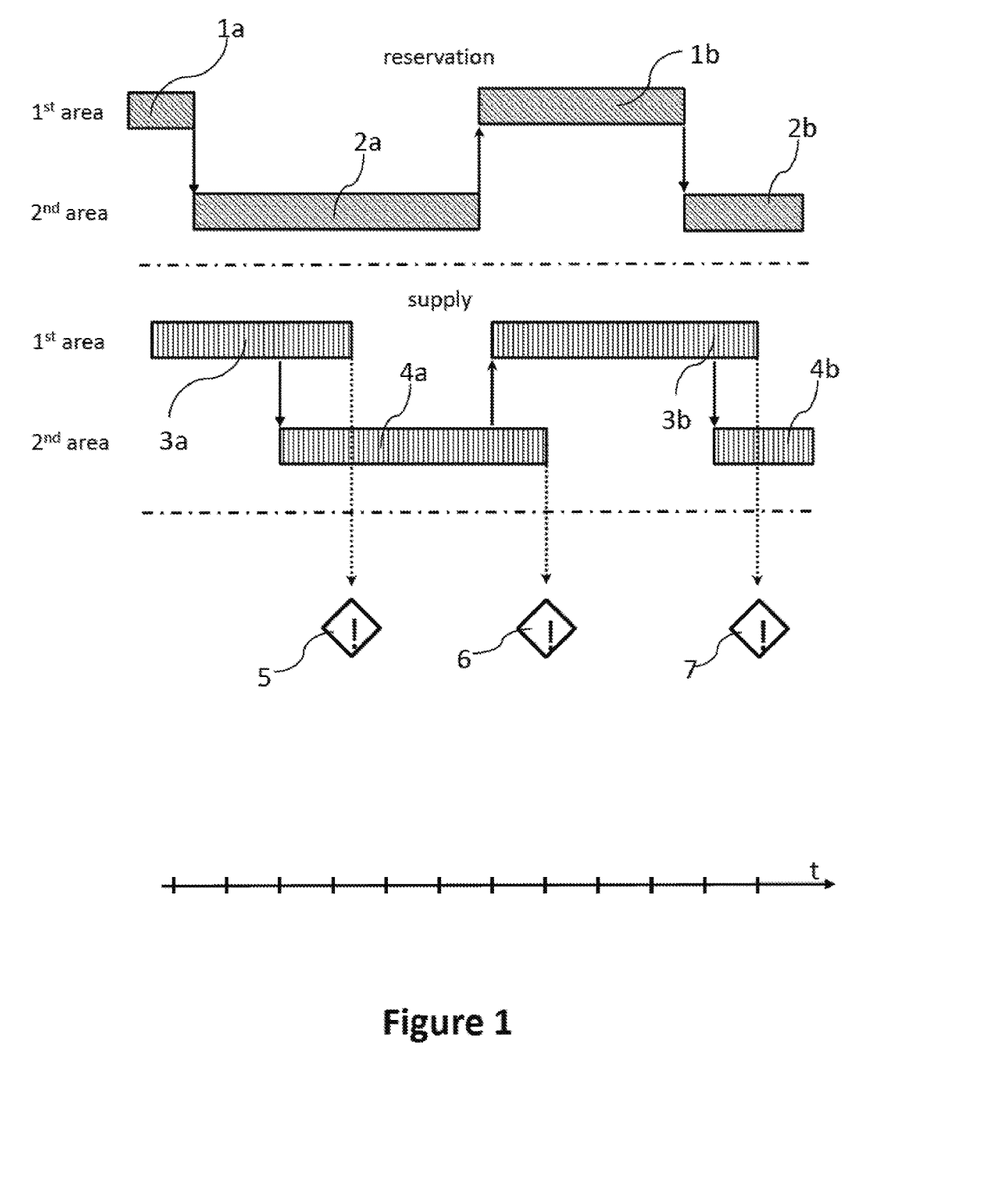
FIG. 1 illustrates a diagram illustrating example reservation and supply operations of a repository of an automated analyzer according to an embodiment of the present disclosure.

FIG. 1 is a diagram illustrating a method for supplying consumable items to an automated sample analyzer. The method can include receiving, by the automated analyzer, one or more orders for analytical tests to be carried out by the analyzer, each of the analytical tests requiring a set of consumable items, reserving 1a, 1b, by the automated analyzer, one or more sets of consumable items corresponding to the one or more sets of consumable items required for the analytical tests in a first storage area (e.g., a first storage compartment) of two or more storage areas of the analyzer, reserving 2a, 2b, by the automated analyzer, one or more sets of consumable items corresponding to the one or more sets of consumable items required for the analytical tests in a second storage area (e.g., a second storage compartment) of the two or more storage areas after one or more predetermined consumable item in the first storage area has been reserved and supplying the reserved consumable items for use in the one or more analytical tests.

FIG. 1 shows a temporal sequence of reservation and supply operations of consumable items for an example with two storage areas of a consumable item repository (further details regarding the structure of the storage areas will be discussed below in connection with FIG. 3 to FIG. 6). The upper part of the diagram depicts how the analyzer switches between the first and the second storage areas for reserving consumable items for later use. In a first period of time 1a, the analyzer can reserve consumable items contained in the first storage area.

In some examples, this can involve one of the following reservation schemes. For instance, the first storage area can include a plurality of consumable items at predefined positions. After having received an order for an analysis procedure (also referenced as 'analytical test' or 'analysis procedure' in the present disclosure), the analyzer can determine that a particular type of consumable item is required for this concrete analysis procedure (e.g., of the set of consumable items required for the particular analysis procedure). The analyzer can then reserve a consumable item of this particular type at a particular position in the first storage area for this analysis procedure. At a later point in time, when the analyzer carries out the scheduled analysis procedure, the analyzer can supply the concrete reserved consumable item from this position. In this manner, the analyzer can keep track of the reserved consumable items in a simplified manner in some examples.

In other examples, the analyzer can merely reserve a particular type of consumable item without reserving a concrete consumable item of this type. For instance, the first storage area can include a certain number of consumable items of a first type (or a certain number of consumable items in total). After the analyzer has received an order for an analysis procedure requiring one or more consumable items of this first type, the analyzer can reserve one or more consumable items in the first storage area without selecting a concrete consumable item. At a later point in time, when the analyzer carries out the scheduled analysis procedure, the analyzer can select a concrete consumable item and supply the concrete consumable to the analysis procedure. In one example, the analyzer only keeps track of an available number of consumable items (or consumable items of a particular type) in a storage area and reserve consumable items by counting down this number.

Regardless of the exact reservation mechanism employed, the analyzer can reserve consumable items in a particular storage area (e.g., the first storage area) until a predefined consumable item in the first storage area has been reserved. This reservation operation can constitute a trigger for the analyzer to switch to the second storage area for subsequent reservations. In other words, the switching to the second area can take place after the predefined consumable item in the first storage area has been reserved.

The predefined consumable item whose reservation triggers the change to another storage area can be selected in a variety of different ways. In one example, the predefined consumable item whose reservation triggers the switching to the second storage area can be a last not reserved consumable item contained in the particular storage area.

In other examples, the predefined consumable item whose reservation triggers the switching to the second storage area can be a last not reserved consumable item of a particular type contained in the particular storage area. For instance, a storage area can include two or more different types of consumable items. In this situation, the one or more predetermined consumable item triggering the switching can be the last consumable item of the first type of consumable items for which a last consumable item is reserved.

In still other examples, the analyzer can carry out a separate reservation process for each of a number of different types of consumable items. For instance, the storage areas of the repository can include two or more different types of consumable items. In this situation, the analyzer can start with reserving the first and second types of consumable items in a first storage area. Then, after a last consumable item of the first type has been reserved in the first storage area, the analyzer can continue with reserving the first type of consumable items in the second storage area. However, the analyzer can continue to reserve consumable items of the second type in the first storage area after this point in time.

Regardless of the details of the switching process, the analyzer can cycle through the switching between the different storage areas for reservation purposes repeatedly (e.g., between a first storage area and a second storage area of the repository). Each switch between the compartments can be triggered by one of the trigger events discussed above. For example, in FIG. 1, the analyzer can switch back to the first storage area after consumable items in the second storage area have been reserved for a second period of time 2a (e.g., after a last consumable item contained in the second storage area has been reserved). Subsequently, the analyzer can reserve consumable items in the first storage area for a third period of time 1b and then can switch to the second storage area again (the first storage area has been replenished in the meantime, as will be discussed below). In the following, the analyzer can reserve consumable items in the second storage area for a fourth period of time 2b. This process can be continued further in the above described manner in some examples.

The timing of the switching between the storage areas for reservation shown in FIG. 1 is purely illustrative and can be different in other examples according to the present disclosure. Depending on the number and/or frequency with which orders for analysis procedures arrive at the analyzer, the duration of the individual reservation periods can vary in length. In some examples, the analyzer can receive a plurality of orders at a certain point in time. For instance, the analyzer can reserve consumable items required to carry out all orders of the plurality of orders (e.g., a fairly large number of consumable items can be reserved within a relatively short period of time). In this situation, the reservation process may start reserving consumable items in the first storage area and switch to the second storage area after a comparatively short period of time.

Irrespective of the details of the reservation process, the reserved consumable items will be supplied for use in the analysis procedure when they are required.

In the following passages, different techniques to synchronize replenishment of the storage areas with the reservation procedure as introduced above will be discussed in more detail. The lower part of FIG. 1 shows an example replenishment sequence according to the present disclosure for an example of two storage areas of a repository for consumable items. The upper row shows periods of time 3a, 3b during which the analyzer can supply consumable items contained in the first storage area to the analysis processes. Accordingly, the lower row shows periods of time 4a, 4b during which the analyzer can supply consumable items contained in the second storage area to the analysis processes. The progress of the supply operation of the consumable items can trigger an indication 5, 6, 7 for a user that a particular storage area can be replenished.

In some examples, an indication that a particular storage area can be replenished is triggered in response to a predetermined consumable can be used in the one or more analytical tests (additional trigger events will be discussed below in connection with FIG. 2). The predetermined consumable item triggering the replenishing indication can be selected in different ways.

In one example, the predetermined consumable item can be a last consumable item contained in a particular storage area. In other examples, the predetermined consumable item can be a last consumable item of a particular type of consumable items contained in the particular storage area. In still other examples, the predetermined consumable item can be a last consumable item of a first type of consumable items for which a last consumable item can be used.

As can be seen in FIG. 1, the supply operations from the first and second storage areas can overlap for a predetermined period of time.

Besides triggering an indication that a particular storage area can be replenished upon occurrence of any one of these trigger events, the analyzer can also switch to a different storage area for supplying the reserved consumable items for use in the one or more analytical tests in some examples. In this manner, it can be secured that the user can carry out the replenishment operation of a first storage area while the analyzer can at the same time supply consumable items for use in an analytical test from a second storage area. This may reduce (and even eliminate in some examples) a down time of the analyzer as situations in which a user interferes with a replenishment process of the automated analyzer can be avoided. However, in other examples (e.g., the examples shown in FIG. 1 or FIG. 2), the replenishment processes from two or more storage areas can overlap for a certain period of time. For instance, supplying operations from a first storage area can still continue for a certain period of time after supplying from a second storage area has commenced.

In still other examples, the analyzer can trigger an indication that a storage area can be replenished when only a predetermined number of consumable items (or a predetermined number of particular types of consumable item) remain in the particular compartment. For example, the analyzer can out output an indication that a particular storage area is low in consumable items. The user can then prepare for replenishing the respective storage area. In this manner, a "dead time" between a user receiving the indication and the actual replenishment operation can be taken into account.

Regardless of the details of the reservation process and the triggering of the replenishment indications, it can be seen in FIG. 1 that the techniques of the present disclosure can allow for a reduced (or even eliminated) idle time of an analyzer by providing a timely warning to a user to replenish the storage areas. On the other hand, a number of individual replenishment operations may be reduced. This may, in turn, reduce an amount of user time required to service the analyzer. For instance, all consumable items in the first storage area may be used at the end of time period 3a. A corresponding indication 5 that the first storage area can be replenished can be triggered at this point in time. As subsequently only consumables of the second storage area can be supplied during a sub-period of a further period of time 4a, a user can have sufficient time to replenish the consumable items in the first storage area. Accordingly, after a last consumable item of the second storage area has been used, the analyzer can trigger a further replenishment indication 6 for the second storage area. This sequence can be repeated for an arbitrary number of times. After a third period of time 3b has elapsed, the consumables of the first storage area have been exhausted again. The user can receive a further replenishment indication 7 for the first storage area.

The timing of the switching for supplying the consumable items shown in FIG. 1 is purely illustrative and can be different in other examples according to the present disclosure. For example, in FIG. 1, there can be an overlap between times in which consumable items are supplied from the first and second storage areas (i.e. periods 3a and 4a can overlap, periods 4a and 3b can overlap, and periods 3b and 4b can overlap). This can happen as a result of reserving consumable items for a plurality of orders at a first (earlier) point in time and carrying out the analytical tests at later points in time. As a result, different analytical tests may be processed in parallel which may require consumable items from both the first and second storage area. However, in other examples, consumable items can be supplied exclusively from the first or second storage area at a predetermined point in time.

In connection with FIG. 1, an example repository including two storage areas has been discussed. However, the techniques of the present disclosure are not limited to a situation with two storage areas. Rather, the techniques can be applied for an arbitrary number of storage areas of an analyzer. For example, in FIG. 2, a situation with five different storage areas containing consumables is illustrated.

Figure 2:
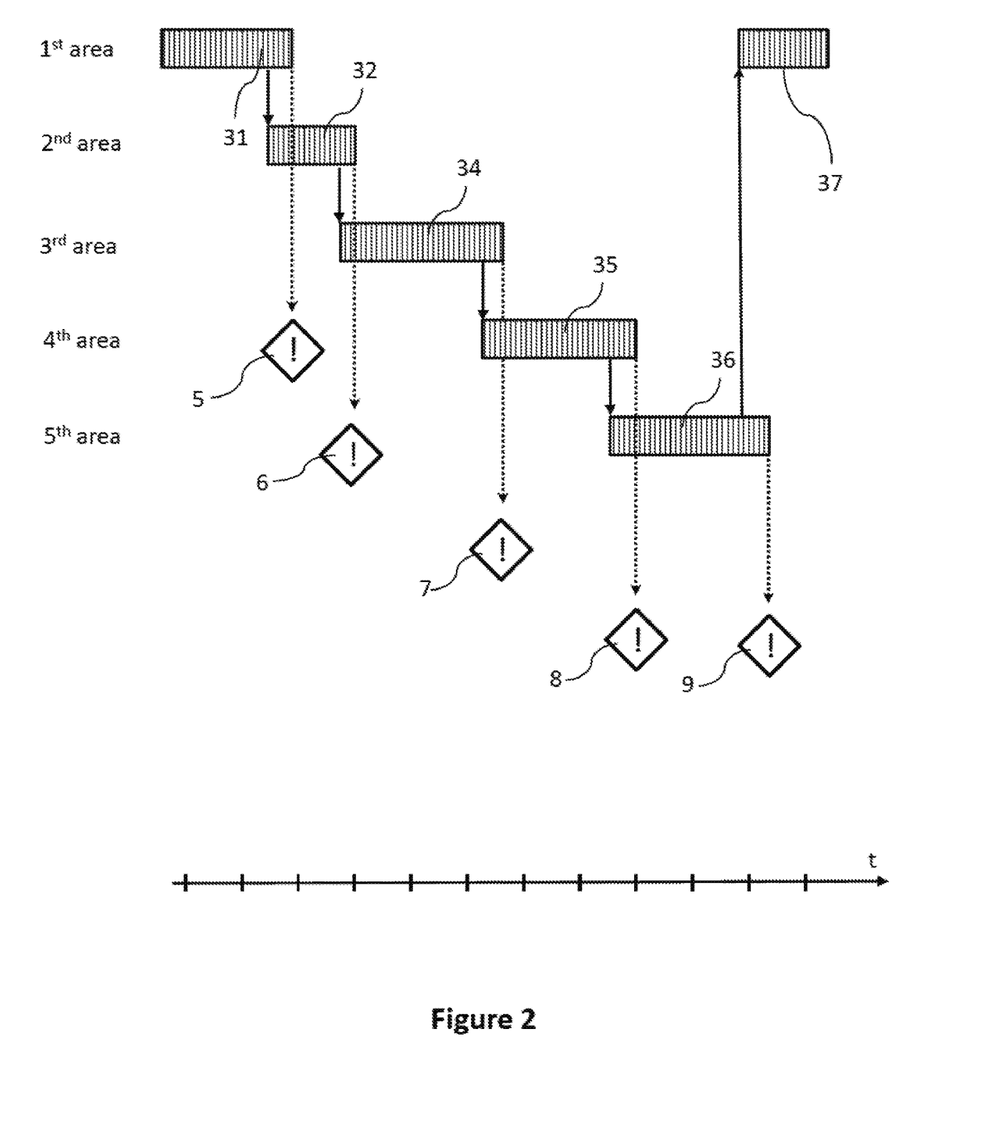
FIG. 2 illustrates a diagram illustrating another example of supply operations of a repository of an automated analyzer according to an embodiment of the present disclosure.

As can be seen in FIG. 2, the analyzer can supply consumable items out of each of the five storage areas in subsequent periods of time 31-37. At the end of each period of time 31-37, the analyzer can detect that a predetermined consumable item is supplied (e.g., a last consumable item contained in the particular storage area or any other consumable item triggering an replenishment indication discussed above in connection with FIG. 1). In response to this detection, a replenishment indication 5-9 can be transmitted to a user.

In parallel, the analyzer can sequentially reserve consumable items in the different storage area. The analyzer can switch between the different storage area in response to one or more of the trigger events discussed above in connection with FIG. 1. In some examples, the analyzer can decide to which storage area to switch next based on evaluating one or more parameters of the plurality of storage areas (e.g., amount of available consumable items in each of the plurality storage areas).

In the example of FIG. 2, the analyzer can generate a replenishment indication 5-9 for each storage area in response to a respective trigger event. In other examples, the analyzer can only generate a replenishment indication in response to a trigger event occurring for the second time (or for the third time or any other predetermined number of times). In still other examples, a replenishment indication can be generated after a predetermined consumable item has been used from all but one storage areas. It may not be necessary to directly replenish the first compartment after a predetermined (e.g., last) consumable item from the first compartment has been used. Rather, a user may wait and replenish multiple compartments in one go.

In the example of FIG. 2, the analyzer can start with a new cycle after consumable items have been supplied from all compartments. In some examples, a sequence in which consumable items are reserved in the multiple storage areas can be different at different times. For example, the order in which consumable items are reserved from the multiple storage areas can be selected based on the type of analysis procedures an analyzer receives. In the subsequent passages, aspects of the replenishment indications can be discussed in more detail.

In one embodiment, the replenishment indication can be any signal to a user that a particular storage area (or a group of storage areas) can be replenished. For example, the replenishment indication can be a visual, audible, or audio-visible signal for the user. In one example, the replenishment indication can be output on a user interface of the analyzer. In other examples, the replenishment indication can be output on a user interface that can be connected to the analyzer through a network. For instance, a control terminal can be coupled to the analyzer receiving the replenishment indication. In addition or alternatively, the user can receive the replenishment indication on a mobile device or another terminal remotely located from the analyzer.

The replenishment indication can include additional information to indicating that a particular storage area can be replenished. For example, the replenishment indication can indicate urgency for the replenishment operation (e.g., by indicating one of a plurality of urgency levels).

For example, a replenishment indication can have a first urgency level directly after the replenishment indication has been generated (e.g., in response to one of the above discussed trigger events). After a predetermined period of time has lapsed or in response to a predetermined event, the replenishment indication can be switched to a second urgency level.

For instance, for an analyzer having two compartments, a replenishment indication can have a first urgency level directly after a last consumable item has been supplied. The user can still have plenty of time to replenish the storage area before the analyzer may have to interrupt its operation. However, upon detecting that a last consumable item of the second storage area has been supplied, the urgency level may be changed. The analyzer risks running out of consumable items so the user should act swiftly.

In the previous passages, replenishment indications directed to users of the analyzer have been discussed. In other examples (or in addition), a replenishment indication can be a signal transmitted to a functional module of the analyzer or another device. In one example, the functional module of the analyzer or the other device can be an automated replenishment device being configured to replenish consumable items in the storage area of the analyzer. For example, the automated replenishment device can be a robotic replenishment device.

In the preceding section, the reservation and replenishment techniques of the present disclosure have been discussed without reference to particular properties of the analyzers. In the following sections example analyzers that can carry out these methods will be discussed.

Figure 3:
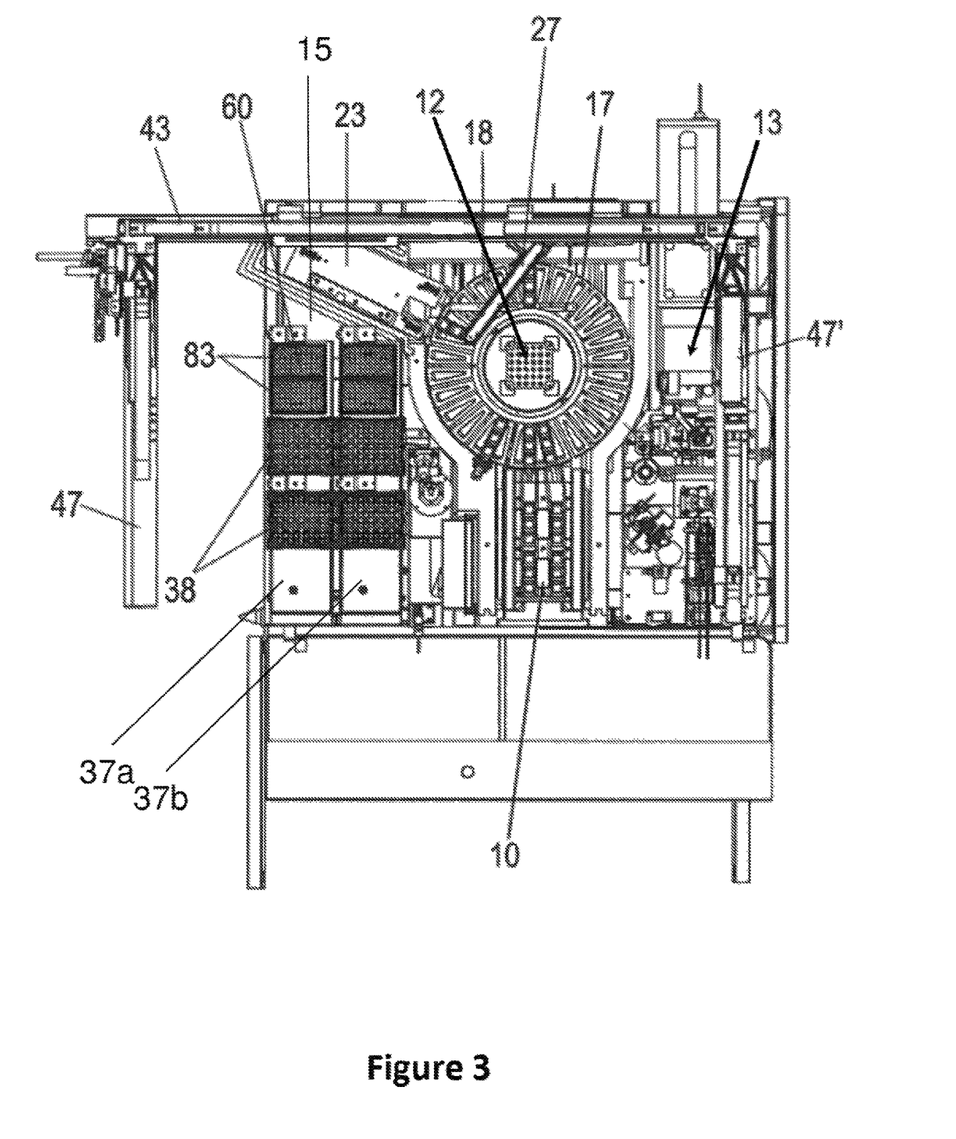
FIG. 3 illustrates an example analyzer including a consumable repository including two storage compartments according to an embodiment of the present disclosure.

FIG. 3 shows an example analyzer including a consumable repository including two storage areas according to the present disclosure. In the example of FIG. 3, the analyzer can be an analyzer for analyzing liquid samples (e.g., a clinical chemistry and immunochemistry analyzer). The analyzer can include a sampling area including a repository of consumable items 15, a sample receiving area (not shown in FIG. 3), analytical area 13 and a reaction area 12. In general, the sample receiving area can include components which can be configured to introduce samples into the analyzer. The reaction area 12 can include components which can be adapted to add one or more reagents to the samples (e.g., reagents necessary for a particular test or assay the analyzer can perform). Last, the analytical area 13 can include components which can be configured to perform one or more analytical tests on the sample.

In the example of FIG. 3, the repository of consumable items 15 can comprises two slidably mounted drawers 37a, 37b (i.e., two storage areas), each of which can be provided with plural recesses for receiving tip racks 38 containing disposable pipetting tips for pipetting fluids and reaction vessel racks 83 containing disposable reaction vessels 60 (i.e., two different types of consumable items). The drawers 37a, 37b can be drawn out of the analyzer at the front-side thereof to be charged with new (filled) tip racks 38 and reaction vessel racks 83, respectively, or uncharged with used (empty) tip racks 38 and reaction vessel racks 83, respectively. By using disposable pipetting tips and disposable reaction vessels 60 (cross-) contamination of liquid samples and reagents can advantageously be avoided.

While two drawers 37a, 37b respectively containing four tip racks 38 and four reaction vessel racks 83 are shown in FIG. 3 for the purpose of illustration, it is to be understood that the analyzer can contain any other number and arrangement of drawers 37a, 37b, tip racks 38 and reaction vessel racks 83 that would be compatible with the analyzer 1 for analyzing liquid samples.

The analyzer can further include two separate two-rail translation systems, i.e., a first translation system and a second translation system, each of which comprising two rails comprised of a common back rail 43 and individual transfer head rails 47, 47', i.e., a first transfer head rail 47 and a second transfer head rail 47', arranged in orthogonal relationship with respect to each other. Furthermore, the first and second transfer head rails 47, 47' respectively can be provided with one transfer head. The transfer heads can be equipped with manipulators (e.g., a gripper and/or a pipettor) for manipulating items stored in the repository, the reaction area and/or the analytical area 13.

The reaction area 12 can include a loader/unloader 10 capable of loading/unloading reagent cassettes to/from holders 18 of a carousel 17 and an analytical area 13 provided with at least one analytical device for analyzing the samples.

The cooperation of these devices of the analyzer can provide for an automated sample preparation and measurement. In particular, the techniques for supplying consumable items described in the present disclosure can be used to supply tips and reaction vessels to the two drawers 37a, 37b.

In connection with FIG. 3, a particular type of analyzer having a particular consumable item repository is shown. Even though the techniques for supplying consumable items can have particular advantages in this setup, the techniques of the present disclosure can equally be applied in other analyzer environments.

For instance, the storage areas can have another layout than a drawer in some examples. In general, the storage area of the present disclosure can include any suitable storage area for storing consumable items in a repository.

In one example, a storage area can be a shelf or a portion of a shelf for storing consumable items. In still other examples, a storage area can include a predetermined surface for storing consumable items. It may not be required that the storage area is adapted to move between a loading position and a position in which the consumable items can be supplied to be used in the analysis processes of the analyzer. For instance, the analyzer of FIG. 3 may not have movable drawers but, instead, two stationary compartments each providing a plurality of storage spaces for tip racks 38 and reaction vessel racks 83.

In still other examples, the storage areas can include movable loading elements other than a drawer. For instance, a movable loading element can be configured to pivot or swivel between a loading position and a position in which the consumable items can be supplied to be used in the analysis processes of the analyzer. In other examples, the movable loading element can move linearly, but in a vertical direction (instead of the horizontal direction in which the drawers 37a, 37b move).

Furthermore, as already discussed above, the techniques of the present disclosure are not limited to supplying reaction vessels and tips but can be used to supply any item that can be consumed by an analyzer for samples in the course of an analysis procedure.

In some examples, the techniques of the present disclosure can be used to supply reagent containers to an analyzer. For example, the analyzer can include two or more storage areas (e.g., reagent carousels) for storing reagents (e.g., reagent cassettes as shown in FIG. 3 or other reagent containers). The analyzer can be configured to apply the techniques described herein to supply reagents to these storage areas. In some examples, a reagent supplying process can be carried out in parallel to a process of supplying other consumable items to the analyzer.

In some examples, as shown in FIG. 3, multiple consumable items of a particular type can be stored in a common container (e.g., a rack, a magazine, a box, a blister or any other suitable container). However, the consumable items can also be provided individually in other examples (e.g., the drawers 37a, 37b of FIG. 3 may be equipped with fixedly installed racks).

In addition or alternatively, the storage areas of the analyzer can be configured to store any number of different types of consumable items. In one example, storage can be configured to store only a single type of consumable item (e.g., a pipette tip or a reaction vessel). In other examples, a compartment can be configured to store three or more or four or more different types of consumable items.

The operations of the analyzer 1 (or of any analyzer described in the present disclosure) can be controlled by a controller (not shown in FIG. 3). In particular, a controller of the analyzer can be configured to carry out the operations of the techniques of the present disclosure.

In one example, the controller can be local at the analyzer (e.g., in a bench-top analyzer). In other examples, the controller can be a remote device remote from other components of the analyzer (e.g., remote from components of the analyzer preparing and/or handling the samples). For instance, a controller can be embodied in a remote computer device connected through a network with the other components of the analyzer. In still other examples, the controller can be located on a remote server or in the cloud. Accordingly, some or all steps of the methods of the present disclosure can be carried out by a local controller or a remote controller (e.g., in the cloud).

According to the present disclosure, a computer-readable medium having instructions stored thereon, which when executed by a controller of an analyzer can make the analyzer performing the steps of any of the methods set out in the present disclosure. Moreover, a signal can have instructions encoded thereon, which when executed by a controller of an analyzer can make the analyzer performing the steps of any of the methods set out in the present disclosure. In one example, an analyzer can be programmed to carry out the techniques of the present disclosure. Even though particular analyzers may not be configured to carry out the techniques of the present disclosure, some analyzers can nevertheless be equipped with the required hardware. In these examples, a software update of the analyzer's software can be sufficient to enable that the respective analyzer carries out the techniques of the present disclosure.

In the preceding sections, several aspects of analyzers of the present disclosure have been discussed in connection with FIG. 3. In the following sections, several aspects of monitoring techniques to keep track of an inventory of consumable items will be discussed in connection with FIG. 4 to FIG. 6.

Figure 4:
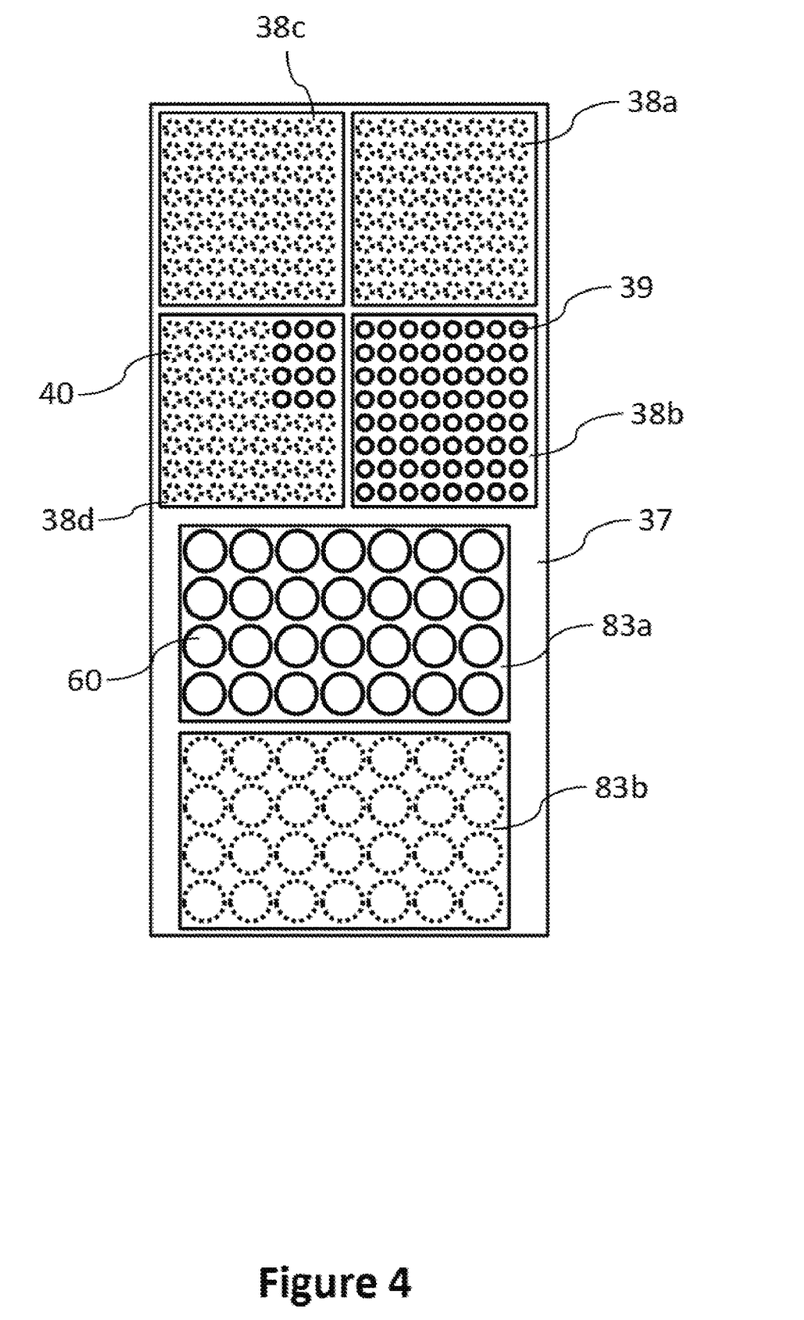
FIG. 4 illustrates an example storage compartment according to an embodiment of the present disclosure.
Figure 5:
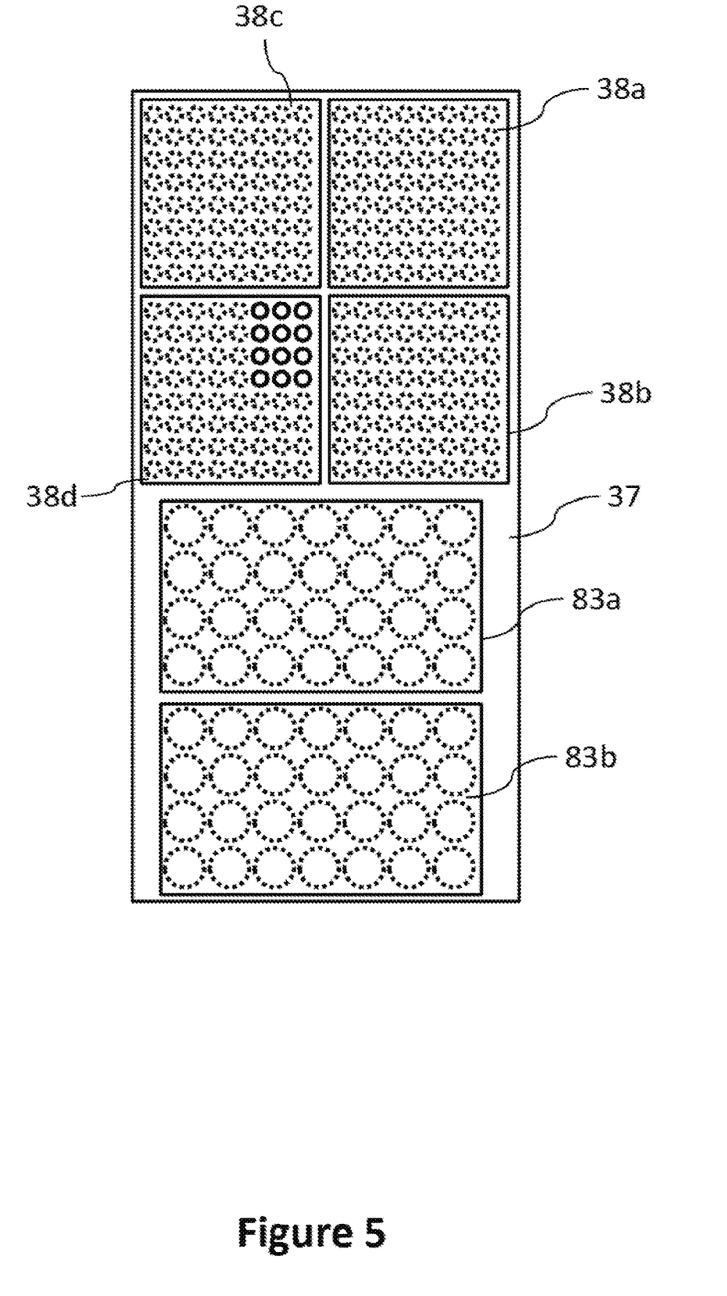
FIG. 5 illustrates an example storage compartment in a state where a replenishment indication is generated according to an embodiment of the present disclosure.
Figure 6:
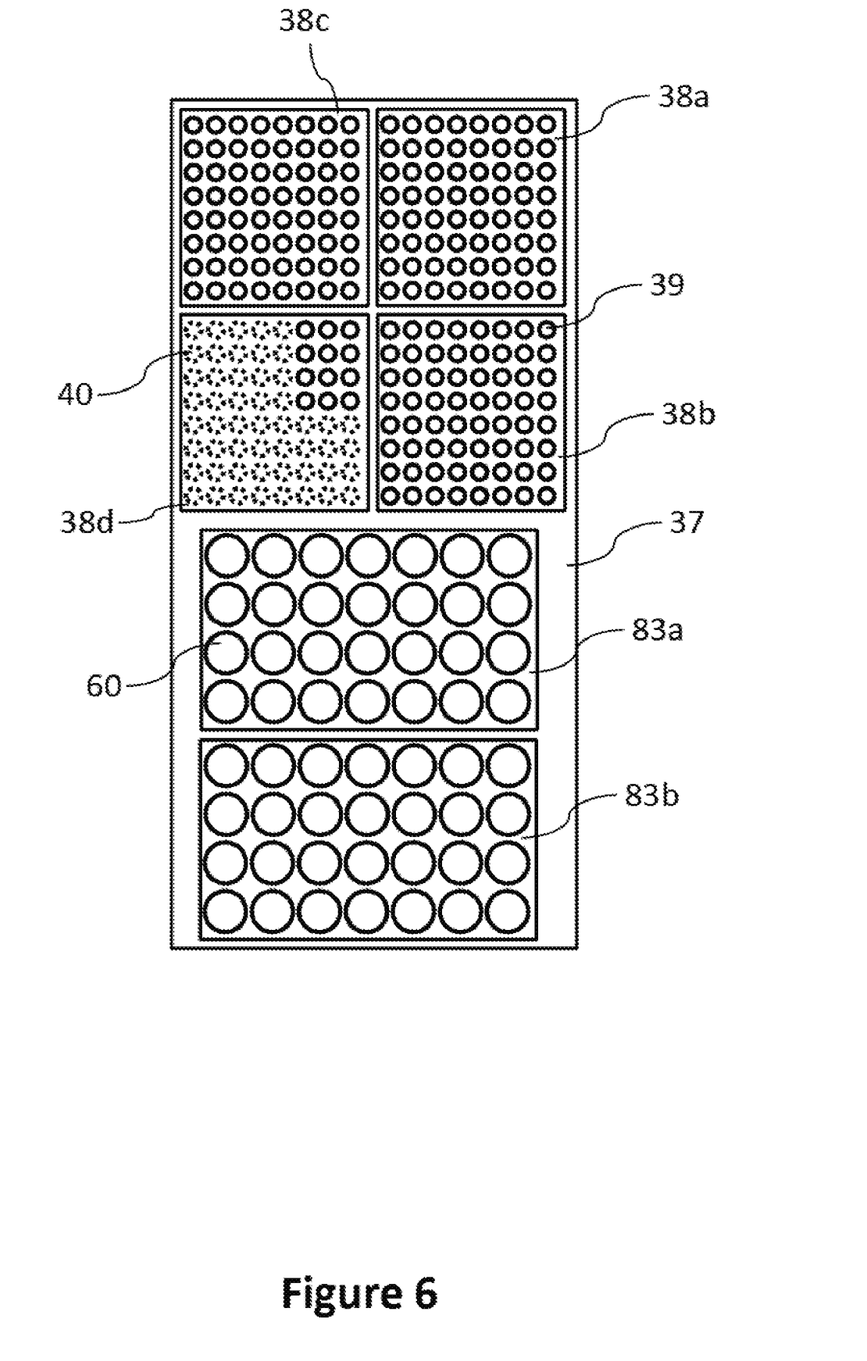
FIG. 6 illustrates an example storage compartment after a user has replenished the storage compartment according to an embodiment of the present disclosure.

FIGS. 4-6 show a storage area 37 of an analyzer for storing consumable items according to the present disclosure. As in FIG. 3, the storage area can be embodied as a drawer and can be configured to store two different types of consumable items 39, 60 contained in corresponding containers 38a-38d, 83a, 83b each storing a plurality of consumable items of a particular type (e.g., racks). In the example of FIG. 4 to FIG. 6, the drawer can include four racks 38a-38d of a first type of consumable items and two racks 83a, 83b of a second type of consumable items for the sake of illustration.

Each container defines a plurality of positions in the storage area which can hold consumable items. In FIG. 4 to FIG. 6, a full circle illustrates a position in a container which can be occupied by a consumable item. A broken circle, on the other hand, illustrates a position which is empty.

In the example analyzer of FIG. 3, the consumable items can be supplied from the positions of the storage areas to an analytical process and afterwards disposed in a separate waste area (not shown in FIG. 3). A user may empty the waste area from time to time.

However, in other analyzer setups, the analyzer can return the used consumable items to the storage areas of the consumable item repository. For instance, the analyzer may return used pipette tips to an empty position in the pipette rack 38a of FIG. 4. In these examples, a position may not be empty but can include a used pipette tip which has to be removed. However, in other examples the consumable items can be transported into a waste area after use in an analysis process.

In general, a position of a storage area (or a position of a container of a storage area) which is either empty or includes an already used consumable items can be labelled as 'used' in the present disclosure. Accordingly, a position of a storage area (or a position of a container of a storage area) which can contain a consumable item which has not been used is labelled as 'not used' or 'unused' in the present disclosure. Containers for multiple consumable items may be 'partially used' if they include used and not used positions.

Coming back to the example of FIG. 4, the vessel tip racks 38a, 38c are used (or empty) and include no further usable vessel tips. The vessel tip rack 38d is partially used and still includes a plurality of unused vessel tips. Last, the vessel tip rack 38b is unused and still is fully stocked with unused vessel tips. In the same manner, FIG. 4 depicts a used reaction vessel rack 83b and an unused reaction vessel rack 83a.

In the situation depicted in FIG. 4, the remaining occupied positions can be reserved for later use in different orders for analysis processes the analyzer can carry out. The analyzer can subsequently supply the reserved vessel tips and reaction vessels so they can be used in carrying out the different orders. For example, a gripper can be configured to grip a reaction vessel 60 stored in one of the reaction vessel racks 83a, 83b and transport it to a position in the analyzer where it can be used in the analysis process. In the same manner, a pipettor can engage with a pipette tip stored in one of the pipette tip racks 38a-38d.

After a certain period of time has elapsed, the drawer 37 may be in the state depicted in FIG. 5. For example, a last reaction vessel may have been supplied to a respective analysis process. At this point in time, the analyzer can generate a replenishment indication to a user, as discussed above. As can be seen, both reaction vessel racks 83a, 83b are completely used in the example of FIG. 5 (in other words, both reaction vessel racks 83a, 83b are empty). Three out of four pipettor tip racks are also used while the last pipettor tip rack 38d is only partially used. Nevertheless, the analyzer may switch to a different storage area to supply consumable items at this point in time. This can avoid that consumable items from two different storage areas have to be supplied. Thus, in the example of FIG. 5 supplying the last consumable item of a particular type of consumable item (e.g., reaction vessels) can trigger the generation of the replenishment indication as well as (in some examples) switching to another storage area for supplying consumable items.

However, in other examples, the analyzer may continue with supplying consumable items from the drawer 37 until the last pipettor tip rack 38d is completely emptied. In the meantime, the analyzer may supply consumable items of a type no longer stored in the drawer 37 from a different drawer (or other storage area). The replenishment indication may be generated when the last consumable item in the drawer has been supplied (e.g., a last pipette tip). In this manner, the drawer is completely emptied before a user is prompted to refill it. In this manner, a number of refill operations may be reduced in some examples.

Upon noticing a replenishment indication, a user may then open the drawer and replenish the consumable items. In some examples, a storage area for storing consumable items may be locked unless the analyzer determines that the respective storage area should be replenished (e.g., upon generation of a replenishment indication). For example, a drawer (or any different storage area) can include an actuatable lock which can be put in a locked state or an unlocked state automatically by the analyzer. In addition or alternatively, a visual indicator associated with the storage area can be activated (e.g., a light in a predetermined color associated with the storage area) in response to the replenishment indication. In this manner, it can be prevented a user from opening the drawer (or other storage area) while consumable items are being supplied from the drawer.

In FIG. 6, a situation is depicted after the user has replenished the drawer 37. As can be seen, the user has refilled five out of the six racks. However, the user has forgotten to replace one of the pipette tip racks 38d by a fully stocked pipette tip rack. In other situations, a user may replace a used or partially used rack (or another container being configured to store a plurality of consumable items) by another used or partially used rack. In order to cope with such situations or other situations in which a user makes a mistake when replenishing the storage areas of consumable items, the analyzers can be configured to monitor the content of the storage area. Aspects of these processes will be discussed subsequently.

In some examples, an analyzer can be configured to monitor a filling state of the two or more storage areas (e.g., a drawer as shown in FIG. 6). For instance, an analyzer can monitor each position configured to hold a consumable item (e.g., by virtue of a camera and by using image recognition technique).

In addition or alternatively, the analyzer can maintain a filling status indicator for each container for consumable items included in the two or more storage compartments of the analyzer. As discussed above, the filling status indicator can have one or more of the states being 'completely used', 'partially used' or 'not used'. For example, in the situation shown in FIG. 5 both reaction vessel containers 83a, 83b may have a state 'completely used.'

Now, after detecting that a user interaction with the compartment has taken place, the analyzer can check whether a filling status indicator of the one or more containers in the storage areas has changed. This can happen in a variety of different ways.

In one example, the analyzer can be configured to, for all containers, checking a consumable item position in each container from which a last consumable item has been supplied to the analysis process. For example, in FIG. 6, the last pipette tip of pipette tip head rack 38b may have been supplied from the position at the lower right corner of the rack 38b. The analyzer may check if this position is occupied (i.e., not used) after a user has replenished the compartment. In FIG. 6 this is the case, so the analyzer can assume that the user properly replenished rack 38b. As a consequence, a filling status indicator for rack 38b can be switched to 'full.'

In the same manner, the last pipette tip of pipette tip head rack 38d may have been supplied from the position at the upper left corner of the rack 38d. The analyzer may check if this position is occupied (i.e., not used) after a user has replenished the compartment. In FIG. 6 this is not the case, the position is still empty (i.e., used). In this case, the analyzer can assume that the user has not replenished rack 38d. As a consequence, a filling status indicator for rack 38b is not switched to 'full.'

In response to detecting an erroneous replenishment, the analyzer can continue with reserving the consumable items in the compartments based on the updated filling status indicators for each container. In addition or alternatively, the analyzer can generate an error message (and, optionally, a warning) upon detecting that one or more of the containers have not been properly replenished.

Regardless of the concrete technique with which a fill state of the compartments is monitored, the analyzer can keep a count of the consumable items (or of each of the consumable items of a particular type) contained in the compartments. This count can be used in the reservation processes described in the present disclosure.

As already discussed above, the storage area of the repositories can be replenished automatically by a correspondingly adapted replenishment device. The replenishment device can take over the tasks of a user described in the respective passages herein. Accordingly, the replenishment indications described herein can be messages which trigger an action of the replenishment device.

In the preceding detailed description multiple examples of methods for supplying consumable items to an automated analyzer for samples and the apparatus for analyzing samples including a consumable item repository have been discussed. However, the methods for supplying consumable items to an automated analyzer for samples and the apparatus for analyzing samples including a consumable item repository can also be configured as set out in the following embodiments.

A method for supplying consumable items to an automated sample analyzer is presented. The automated analyzer can include a consumable repository including two or more storage areas. Each storage area can be configured to store a plurality of consumable items. The method can comprise receiving one or more orders for analytical tests to be carried out by the analyzer. Each of the analytical tests can require a set of consumable items. The method can also comprise reserving consumable items corresponding to the one or more sets of consumable items required for the analytical tests in a first area of the two or more storage areas, switching to a second storage area of the two or more storage areas for reserving consumable items in response to determining that a predetermined consumable item in the first storage area has been reserved, supplying the reserved consumable items for use in the one or more analytical tests, and indicating that the first storage area can be replenished in response to determining that a particular consumable item of the first storage area has been used in the one or more analytical tests.

The particular consumable item triggering an indication that the first storage area can be replenished can be a last consumable item contained in the first storage area. The particular consumable item triggering an indication that the first storage area can be replenished can be a last consumable item of a predetermined type contained in the first storage area.

The first and second storage areas can be first and second storage compartments. The first and second storage compartments can include first and second drawers for storing the consumable items.

The predetermined consumable item whose reservation triggers a switching to a second storage area can be a last not reserved consumable item in the first storage area.

The predetermined consumable item whose reservation triggers a switching to a second storage area can be a last not reserved consumable item of a predetermined type in the first storage area.

Reserving the sets of consumable items required for the analytical tests can include reserving concrete consumable items contained in the respective storage area. Reserving a concrete consumable item can include reserving a consumable item stored at a particular position in the respective storage area. Reserving the sets of consumable items required for the analytical tests can include reserving an arbitrary consumable item of a required type contained in the respective storage area.

A concrete consumable item can only be selected upon supplying the reserved consumable item for use in the one or more analytical tests.

The consumable items can include one or more of instrument tips, sample vessels, reaction vessels, needles, and reagent containers. The reaction vessel, the transport vessel or the sample vessel can be a cuvette, a tube, a slide, a multiwell plate or microplate. The instrument tip can be a pipette tip.

At least some of the consumable items can be arranged in a plurality of containers each being configured to contain two or more consumable items. The containers can include one or more of a rack, a magazine.

The method can also comprise scheduling the one or more orders for analytical tests to be carried out by the analyzer in a schedule before reserving consumable items for the respective analytical tests. The schedule can define an order in which the analytical tests can be carried out.

The method can also comprise reserving the consumable items according to the order laid out in the schedule.

The method can also comprise monitoring a filling state of the two or more storage areas. The consumable items can be arranged in a plurality of containers each being configured to contain two or more consumable items. Monitoring the filling status of the two or more storage areas can include maintaining a filling status indicator for each of the containers. The filling status indicator can have one or more of the states completely used, partially used or not used.

Monitoring the filling status can include, for all containers which are supposed to include at least some not used positions, checking a consumable item position in a container which have been used in the one or more analytical tests, and, if the position contains a consumable item, changing the status to not used. A monitoring action can be triggered upon detecting that a user interaction with the respective storage area has taken place.

The method can also comprise logging a filling status of the two or more storage areas and/or of containers each including a plurality of consumable items stored in the two or more storage areas. Logging the filling status can include counting a number of each particular type of consumables stored in the repository.

Indicating that the first storage area can be replenished can include generating a message for a user of the automated analyzer. Generating a message can include generating a visual, audible, or audio-visible signal for the user.

A locking closing mechanism of the first storage area can be unlocked when the first storage area can be replenished.

The method can further comprise receiving a user input indicating lot information of a lot of consumable items stored in the repository.

The consumable repository can include more than two storage areas. Each storage area can be configured to store a plurality of consumable items.

The method can further comprise reserving one or more sets of consumable items corresponding to the one or more sets of consumable items required for the analytical tests in a further storage area of the more than two storage areas in response to detecting that a predetermined consumable item in the second storage area has been reserved.

The method can further comprise switching back to first storage area of the two or more storage areas for reserving consumable items in response to detecting that a predefined consumable item in the second storage area has been reserved.

The indicating that the first storage area can be replenished includes issuing an electronic signal to an automated replenishment system. The automated replenishment system can be part of the automated analyzer or part of a device external to the automated analyzer.

A method for monitoring a repository of consumable items of an automated sample analyzer is presented. The consumable repository can include at least one storage area. The at least one storage area can be configured to store a plurality of consumable items in one or more containers. Each container can be configured to contain two or more consumable items. The method can comprise logging a filling status of each of the containers, detecting an interaction of a user or an automated refilling device with the at least one storage area, and checking, for each container, a predetermined position in the container from which a consumable item has been used in the one or more analytical tests prior to the interaction with the at least one storage area. If the predetermined position includes a non-used consumable item, a filling status of the respective container can be changed to not used.

The predetermined position can be a last position from which a consumable item has been supplied for use in the one or more analytical tests prior to the user interaction.

The interaction with the at least one storage area can include a replenishment action of a user or an automated refilling device.

An apparatus for analyzing samples is presented. The apparatus can include a consumable repository including two or more storage areas. Each storage area can be configured to store a plurality of consumable items. The apparatus can also include a supply device for supplying the consumable items to be used in the analysis processes and a controller configured to control the apparatus to perform the above methods The apparatus can further comprise a user interface for outputting status messages to a user.

At least one of the two or more storage areas can be a drawer.

A computer-readable medium having instructions stored thereon, which when executed by a controller of an analyzer can control the analyzer to perform the above methods.

Further disclosed and proposed is a computer program including computer-executable instructions for performing the method according to the present invention in one or more of the embodiments enclosed herein when the program can be executed on a computer or computer network. Specifically, the computer program may be stored on a computer-readable data carrier. Thus, specifically, one, more than one or even all of method steps as disclosed herein may be performed by using a computer or a computer network, preferably by using a computer program.

Further disclosed and proposed is a computer program product having program code, in order to perform the method according to the present invention in one or more of the embodiments enclosed herein when the program is executed on a computer or computer network. Specifically, the program code may be stored on a computer-readable data carrier.

Further disclosed and proposed is a data carrier having a data structure stored thereon, which, after loading into a computer or computer network, such as into a working memory or main memory of the computer or computer network, may execute the method according to one or more of the embodiments disclosed herein.

Further disclosed and proposed is a computer program product with program code stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Further disclosed and proposed is a modulated data signal which contains instructions readable by a computer system or computer network, for performing the method according to one or more of the embodiments disclosed herein.

Referring to the computer-implemented aspects, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing measurements.

Further disclosed and proposed is a computer or computer network comprising at least one processor, wherein the processor is adapted to perform the method according to one of the embodiments described in this description.

Further disclosed and proposed is a computer loadable data structure that is adapted to perform the method according to one of the embodiments described in this description while the data structure is being executed on a computer.

Further disclosed and proposed is a storage medium, wherein a data structure is stored on the storage medium and wherein the data structure is adapted to perform the method according to one of the embodiments described in this description after having been loaded into a main and/or working storage of a computer or of a computer network.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method for supplying consumable items to an automated sample analyzer, wherein the automated analyzer includes a consumable repository including two or more storage areas, each storage area being configured to store a plurality of consumable items, the method comprises:

receiving one or more orders for analytical tests to be carried out by the analyzer, each of the analytical tests requiring a set of consumable items;

reserving consumable items corresponding to the one or more sets of consumable items required for the analytical tests in a first storage area of the two or more storage areas of the analyzer;

switching to a second storage area of the two or more storage areas of the analyzer for reserving consumable items in response to determining that a predetermined consumable item in the first storage area has been reserved;

supplying the reserved consumable items for use in the one or more analytical tests; and indicating that the first storage area can be replenished in response to determining that a particular consumable item of the first storage area has been used in the one or more analytical tests while the analyzer continues to supply consumable items from the second storage area.

2. The method of claim 1, wherein the particular consumable item triggering an indication that the first storage area can be replenished is a last consumable item contained in the first storage area.

3. The method of claim 1, wherein the particular consumable item triggering an indication that the first storage area can be replenished is a last consumable item of a predetermined type contained in the first storage area.

4. The method of claim 1, wherein the first and second storage areas are first and second storage compartments.

5. The method of claim 4, wherein the first and second storage compartments include first and second drawers for storing the consumable items.

6. The method of claim 1, wherein the predetermined consumable item whose reservation triggers a switching to a second storage area is a last not reserved consumable item available for reservation in the first storage area.

7. The method of claim 1, wherein the predetermined consumable item whose reservation triggers a switching to a second storage area is a last not reserved consumable item of a predetermined type available for reservation in the first storage area.

8. The method of claim 1, wherein reserving the sets of consumable items required for the analytical tests includes reserving concrete consumable items contained in the respective storage area.

9. The method of claim 1, wherein at least some of the consumable items are arranged in a plurality of containers, each being configured to contain two or more consumable items.

10. The method of claim 1, further comprising,
scheduling the one or more orders for analytical tests to be carried out by the analyzer in a schedule before reserving consumable items for the respective analytical tests, the schedule defining an order in which the analytical tests shall be carried out; and
reserving the consumable items according to the order laid out in the schedule.

11. The method of claim 1, further comprising,
monitoring a filling state of the two or more storage areas, wherein the consumable items are arranged in a plurality of containers each being configured to contain two or more consumable items and wherein monitoring the filling status of the two or more storage areas includes maintaining a filling status indicator for each of the containers.

12. The method of claim 11, wherein monitoring the filling status includes, for all containers which are supposed to include at least some not used positions, checking a consumable item position in a container which has been used in the one or more analytical tests, and, if the position contains a consumable item, changing the status to not used.

13. The method of claim 1, wherein indicating that the first storage area can be replenished includes generating a message for a user of the automated analyzer.

14. The method of claim 1, wherein generating a message generates a visual, audible, or audio-visible signal for the user.

15. The method of claim 1, wherein a locking closing mechanism of the first storage area is unlocked when the first storage area can be replenished.

16. The method of claim 1, wherein the indicating that the first storage area can be replenished includes issuing an electronic signal to an automated replenishment system.

17. An apparatus for analyzing samples, the apparatus comprising:
a consumable repository including two or more storage areas, each storage area being configured to store a plurality of consumable items;
a supply device for supplying the consumable items to be used in the analysis processes; and
a controller configured to control the apparatus to perform the steps of the method of claim 1.

18. A computer-readable medium having instructions stored thereon, which when executed by a controller of an analyzer controls the analyzer to perform the steps of the method of claim 1.

* * * * *